US012789017B2

(12) United States Patent
Chen et al.

(10) Patent No.: US 12,789,017 B2
(45) Date of Patent: Nov. 10, 2026

(54) TREATMENT HANDPIECE, TREATMENT TIP AND ULTRASONIC THERAPEUTIC APPARATUS

(71) Applicant: SHENZHEN PENINSULA MEDICAL GROUP, Shenzhen (CN)

(72) Inventors: Fei Chen, Shenzhen (CN); Lianjun Liu, Shenzhen (CN); Yujia Peng, Shenzhen (CN); Xiaobing Lei, Shenzhen (CN)

(73) Assignee: SHENZHEN PENINSULA MEDICAL GROUP, Shenzhen (CN)

(*) Notice: Subject to any disclaimer, the term of this patent is extended or adjusted under 35 U.S.C. 154(b) by 67 days.

(21) Appl. No.: 18/816,299

(22) Filed: Aug. 27, 2024

(65) Prior Publication Data

US 2025/0001218 A1 Jan. 2, 2025

Related U.S. Application Data

(63) Continuation of application No. PCT/CN2024/101682, filed on Jun. 26, 2024.

(30) Foreign Application Priority Data

Jun. 27, 2023 (CN) ......................... 202310771224.1
Jun. 27, 2023 (CN) ......................... 202310773202.9
Jun. 27, 2023 (CN) ......................... 202321660786.0

(51) Int. Cl.
*A61N 7/00* (2006.01)

(52) U.S. Cl.
CPC ........ *A61N 7/00* (2013.01); *A61N 2007/0008* (2013.01)

(58) Field of Classification Search
CPC ........................................................ A61N 7/00
See application file for complete search history.

(56) References Cited

U.S. PATENT DOCUMENTS 10,806,538 B2 * 10/2020 Farritor ................ A61B 90/361
11,883,065 B2 * 1/2024 Frederick ........... A61B 17/0218
(Continued)

FOREIGN PATENT DOCUMENTS

CN 202154700 U 3/2012
CN 102630154 A 8/2012
(Continued)

OTHER PUBLICATIONS

International Search Report and Written Opinion issued in corresponding PCT Application No. PCT/CN2024/101682, dated Sep. 14, 2024.

(Continued)

*Primary Examiner* — Joanne M Rodden
(74) *Attorney, Agent, or Firm* — Westbridge IP LLC

(57) ABSTRACT

Disclosed are a treatment handpiece and a treatment tip, and an ultrasonic therapeutic apparatus. The treatment handpiece includes a handpiece body and a treatment tip, the handpiece body includes a driving assembly and an output shaft, one end of the output shaft is connected to the driving shaft of the driving assembly, and the first end of the output shaft is provided with a first guiding element. The treatment tip includes a transducer assembly and an input shaft, one end of the input shaft is connected to the transducer assembly, and the other end of the input shaft is provided with a second guiding element; when the first end of the output shaft is connected to the other end of the input shaft, the first guiding element is connected to the second guiding element.

18 Claims, 10 Drawing Sheets

10

(56) References Cited

U.S. PATENT DOCUMENTS

| | | | | |
|---|---|---|---|---|
| 11,903,658 | B2 * | 2/2024 | Farritor | A61B 34/30 |
| 12,156,710 | B2 * | 12/2024 | Wilson | A61B 34/37 |
| 2005/0021069 | A1 * | 1/2005 | Feuer | A61M 29/02 606/192 |
| 2014/0228820 | A1 * | 8/2014 | Blaskowski | A61B 17/00 606/1 |
| 2015/0031991 | A1 * | 1/2015 | Elfar | A61B 10/0233 604/117 |
| 2015/0297178 | A1 * | 10/2015 | Deladi | A61N 7/022 29/525.01 |
| 2016/0338781 | A1 | 11/2016 | Kapadia | |
| 2017/0303895 | A1 | 10/2017 | Park et al. | |
| 2018/0044080 | A1 * | 2/2018 | Presche | B65D 41/28 |
| 2019/0142247 | A1 * | 5/2019 | Maeda | A61B 1/018 600/106 |
| 2019/0282834 | A1 * | 9/2019 | Zawada | A61B 90/361 |
| 2019/0321262 | A1 * | 10/2019 | Chudek | A61J 1/2037 |
| 2020/0100853 | A1 | 4/2020 | Ho et al. | |
| 2021/0085396 | A1 * | 3/2021 | Kawamura | A61B 18/28 |
| 2022/0015795 | A1 * | 1/2022 | Nie | A61B 17/320092 |

FOREIGN PATENT DOCUMENTS

| | | | | |
|---|---|---|---|---|
| CN | 102793567 | A | 11/2012 | |
| CN | 104399191 | A | 3/2015 | |
| CN | 105943177 | A | 9/2016 | |
| CN | 106618636 | A | 5/2017 | |
| CN | 211749907 | U | 10/2020 | |
| CN | 112438757 | A | 3/2021 | |
| CN | 213347509 | U | 6/2021 | |
| CN | 216903352 | U | 7/2022 | |
| CN | 115445111 | A | 12/2022 | |
| CN | 219071880 | U | 5/2023 | |
| CN | 116637309 | A | 8/2023 | |
| CN | 116726417 | A | 9/2023 | |
| CN | 220370316 | U | 1/2024 | |
| EP | 4023184 | A1 | 7/2022 | |
| JP | 2006258277 | A | 9/2006 | |
| JP | 2018500075 | A | 1/2018 | |
| JP | 2022045919 | A | 3/2022 | |
| KR | 20170015269 | A | 2/2017 | |
| WO | WO-2016085051 | A1 * | 6/2016 | G01S 7/521 |
| WO | 2023284507 | A1 | 1/2023 | |

OTHER PUBLICATIONS

First Office Action issued in counterpart Chinese Patent Application No. 202310773202.9, dated Jan. 14, 2026.

Notice of Reasons for Refusal issued in counterpart Japanese Patent Application No. 2024-577312, dated Dec. 23, 2025.

European Search Report issued in counterpart European Patent Application No. EP 24821245.8, dated Jun. 22, 2026.

First Office Action issued in counterpart Chinese Patent Application No. 202310771224.1, dated Jun. 12, 2026.

Notice of Reasons for Refusal issued in counterpart Japanese Patent Application No. 2024-577312, dated Jul. 7, 2026.

Second Office Action issued in counterpart Chinese Patent Application No. 202310773202.9, dated May 21, 2026.

* cited by examiner

TREATMENT HANDPIECE, TREATMENT TIP AND ULTRASONIC THERAPEUTIC APPARATUS

CROSS-REFERENCE TO RELATED APPLICATIONS

This application is a continuation application of International Application No. PCT/CN2024/101682, filed on Jun. 26, 2024, which claims priority to Chinese Patent Application No. 202310771224.1, filed on Jun. 27, 2023, Chinese Patent Application No. 202321660786.0, filed on Jun. 27, 2023, and Chinese Patent Application No. 202310773202.9, filed on Jun. 27, 2023. The disclosures of the above-mentioned applications are incorporated herein by reference in their entireties.

TECHNICAL FIELD

The present application relates to the technical field of ultrasonic therapy, and in particular to a treatment handpiece and a treatment tip, and an ultrasonic therapeutic apparatus.

BACKGROUND

Ultrasound refers to mechanical vibration waves with a frequency of more than 20,000 Hz that cannot cause auditory response in normal people. The method of applying ultrasound energy to the human body to achieve therapeutic purposes is called ultrasound therapy.

Ultrasonic therapeutic apparatus is a therapeutic apparatus that focuses ultrasound on the subcutaneous fat layer to generate high heat, destroy subcutaneous fat cells, and play a fat-reducing role. The treatment handpiece of the existing ultrasonic therapeutic apparatus usually includes a treatment tip and a handpiece. The input shaft of the treatment tip and the output shaft of the handpiece need to be manually aligned and connected, which is time-consuming and affects efficiency.

SUMMARY

The main purpose of the present application is to provide a treatment handpiece including a treatment tip and a handpiece body, which intends to quickly connect the treatment tip and the handpiece body, thus improving work efficiency.

To achieve the above purpose, the treatment handpiece proposed in the present application includes a handpiece body and a treatment tip. The handpiece body includes a driving assembly, the driving assembly is provided with a rotatable output shaft, and a first end of the output shaft is provided with a first guiding element; the treatment tip includes a transducer assembly and an input shaft, one end of the input shaft is connected to the transducer assembly, and the other end of the input shaft is provided with a second guiding element; and the first guiding element is connected and installed with the second guiding element such that the output shaft drives the input shaft to rotate while the input shaft drives the transducer assembly to move linearly.

The present application proposes a treatment tip including an input shaft and a transducer. The transducer motion assembly includes a rotary motion part and a linear motion part, one end of the input shaft is connected to the rotary motion part, and the linear motion part is connected to the rotary motion part; the transducer is connected to the linear motion part; and the input shaft drives the rotary motion part to rotate while the rotary motion part drives the linear motion part to linearly move, such that the transducer moves linearly.

The present application further proposes an ultrasonic therapeutic apparatus, which includes the treatment handpiece described above.

BRIEF DESCRIPTION OF THE DRAWINGS

In order to explain the embodiments of the present application or the technical solutions in the existing technology more clearly, the accompanying drawings needed to be used in the description of the embodiments or the existing technology will be briefly introduced below. Obviously, the accompanying drawings in the following description are only some embodiments of the present application, other accompanying drawings can be obtained based on the provided accompanying drawings without exerting creative efforts for those of ordinary skill in the art.

Figure 1:
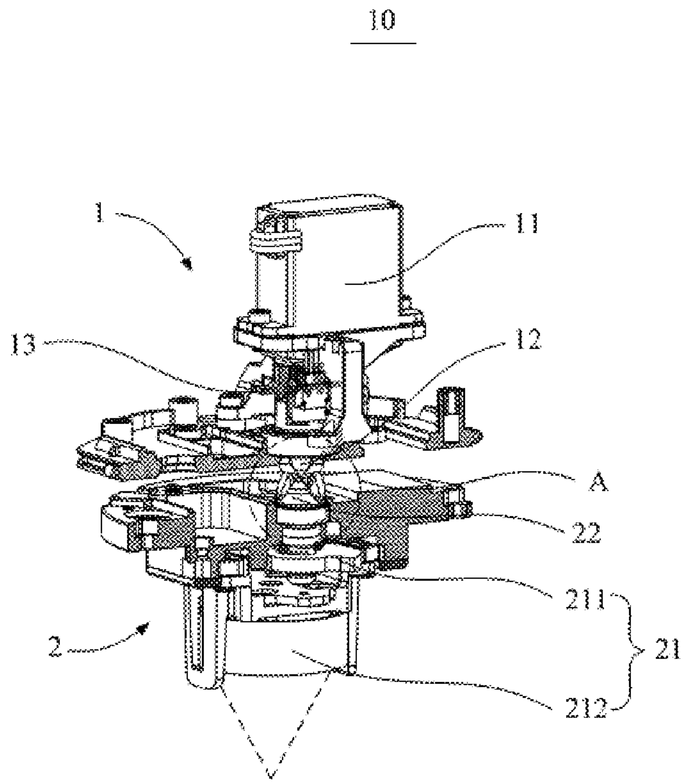
FIG. 1 is a structural schematic view of a treatment handpiece according to an embodiment of the present application.
Figure 2:
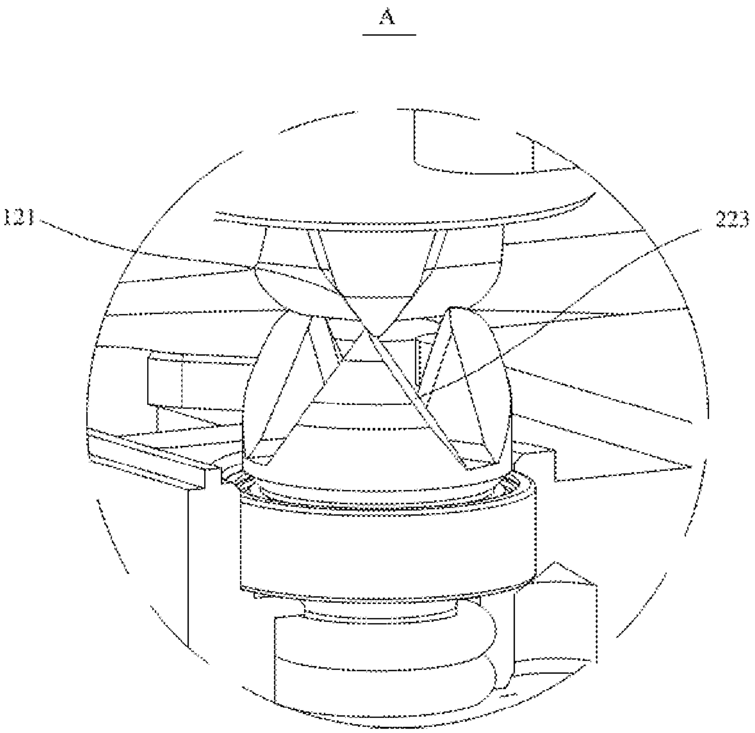
FIG. 2 is a partial enlarged view at position A in FIG. 1.
Figure 3:
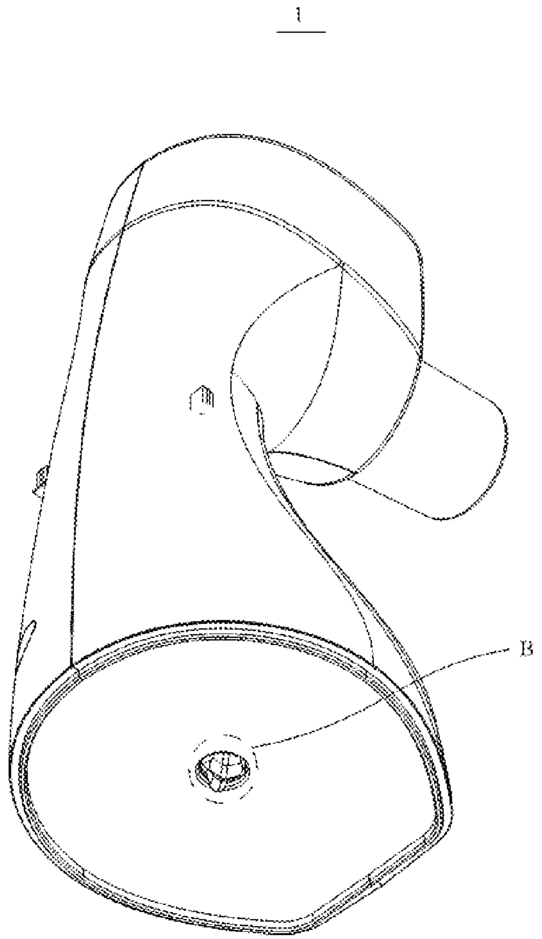
FIG. 3 is a structural schematic view of a handpiece body according to an embodiment of the present application.
Figure 4:
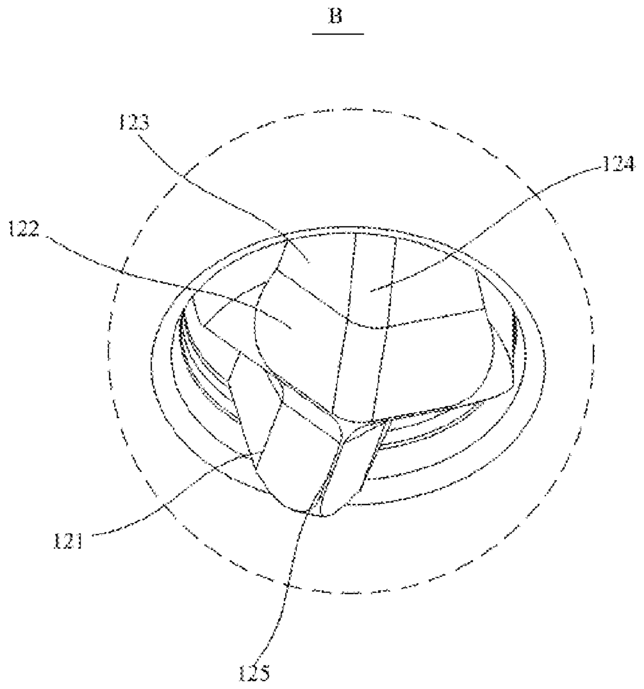
FIG. 4 is a partial enlarged view at position B in FIG. 3.
Figure 5:
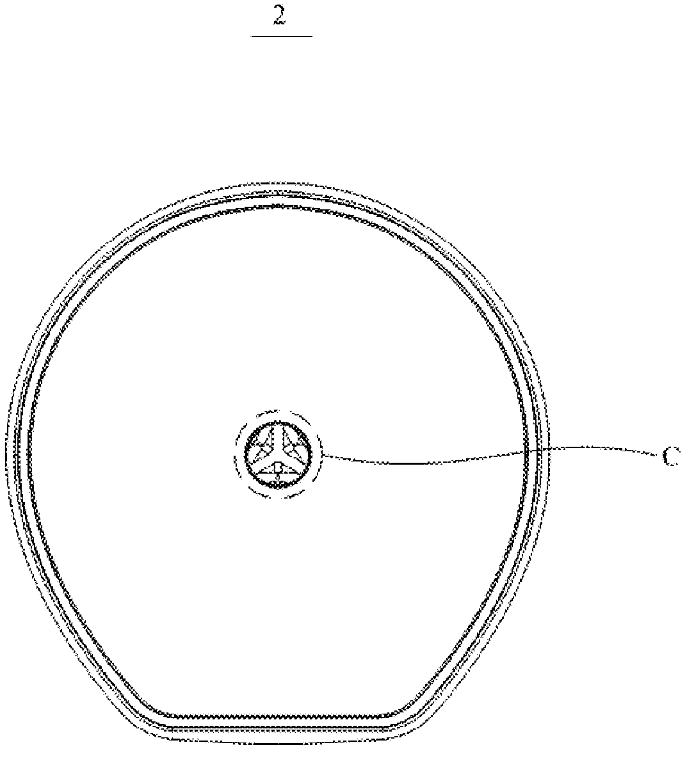
FIG. 5 is a top view of a treatment tip according to an embodiment of the present application.
Figure 6:
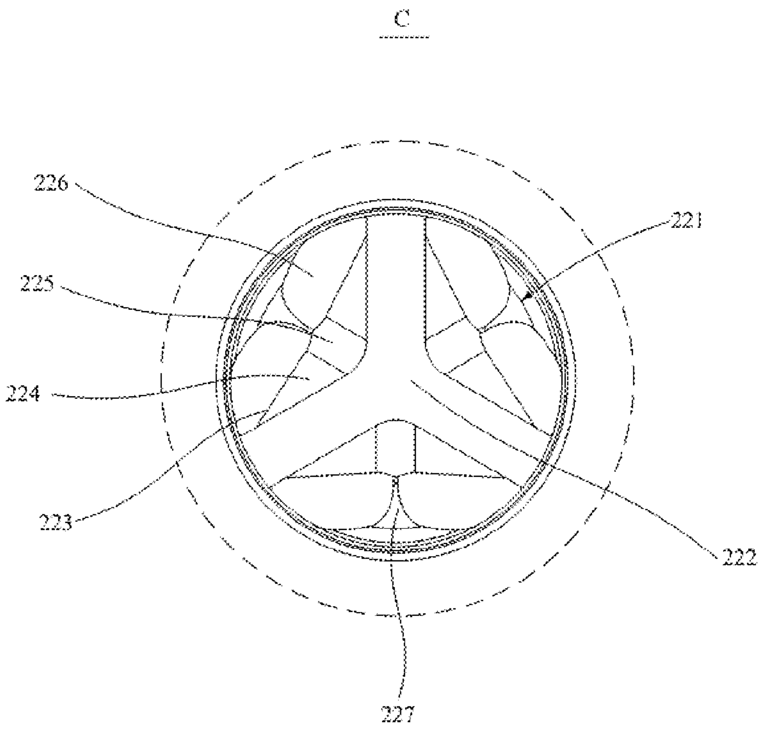
FIG. 6 is a partial enlarged view at position C in FIG. 5.

The realization of the purpose, functional features and advantages of the present application will be further described in conjunction with the embodiments and with reference to the accompanying drawings.

DETAILED DESCRIPTION OF THE EMBODIMENTS

The technical solutions in the embodiments according to the present application will be clearly and completely described below in conjunction with the accompanying drawings in the embodiments according to the present application, and it is clear that the described embodiments are only a part of the embodiments according to the present application, and not all of the embodiments. Based on the embodiments in the present application, all other embodiments obtained by those skilled in the art without making creative labor fall within the scope of the present application.

It should be noted that if there are directional instructions (such as up, down, left, right, front, back or the like) involved in the embodiments of the present application, the directional indications are only configured to explain the relative positional relationship, movement and so on between various components in a specific posture (as shown in the accompanying drawings). If the specific posture changes, the directional indication will also change accordingly.

In addition, in the embodiment of the present application, if there are descriptions involving "first", "second" or the like, the descriptions of "first", "second" or the like are only for descriptive purposes and cannot be understood as indicating or implying the relative importance or implicitly indicating the quantity of the technical features indicated. Therefore, features defined as "first" and "second" may explicitly or implicitly include at least one of these features. In addition, the meaning of "and/or" appearing in the entire text includes three parallel solutions, taking "A and/or B" as an example, it includes solution A, or solution B, or a solution that satisfies both A and B at the same time. In addition, the technical solutions of various embodiments can be combined with each other, but it is based on that those of ordinary skill in the art can realize. When the combination of technical solutions is contradictory or cannot be realized, it should be considered that such combination of technical solutions does not exist and is not within the protection scope claimed by the present application.

The treatment handpiece of the existing ultrasonic therapeutic apparatus usually includes a treatment tip and a handpiece. The input shaft of the treatment tip and the output shaft of the handpiece need to be manually aligned and connected, which is time-consuming and affects efficiency. Therefore, the present application provides a treatment handpiece that can quickly install the handpiece body and the treatment tip.

The present application proposes a handpiece body 10 including a driving assembly 1 and a treatment tip 2. The handpiece body 1 includes a driving assembly 11, the driving assembly is provided with a rotatable output shaft 12, and a first end of the output shaft 12 is provided with a first guiding element. The treatment tip 2 includes a transducer assembly 21 and an input shaft 22, one end of the input shaft 22 is connected to the transducer assembly 21, and the other end of the input shaft 22 is provided with a second guiding element. The first end of the output shaft 12 is opposite to the other end of the input shaft 22. The first guiding element is connected and installed with the second guiding element such that the output shaft 12 drives the input shaft 22 to rotate while the input shaft 12 drives the transducer assembly 21 to move linearly.

In this embodiment, the driving assembly 11 is configured to drive the output shaft 12 to rotate, and can be a driving device such as a stepper motor or a servo motor, or other rotating devices that can drive the output shaft 12 to rotate, and no further limitation is made here. The input shaft 22 and the output shaft 12 are both made of metal materials, such as stainless steel, titanium alloy, etc., which are strong and wear-resistant. The transducer assembly 21 includes a transducer motion assembly 19 and a transducer body 212. The transducer motion assembly 19 is connected to the input shaft 22, and can convert the rotary motion of the input shaft 22 into a linear reciprocating motion, and drive the transducer body 212 to perform a linear reciprocating motion, so as to achieve the planar treatment effect of the treatment handpiece 10. A first guiding element is formed at the other end of the output shaft 12, and a second guiding element is formed at the other end of the input shaft 22. When assembling the handpiece body 1 and the treatment tip 2, the first guiding element on the output shaft 12 abuts against the second guiding element on the input shaft 22, and then the first guiding element and the second guiding element slide relative to each other to achieve a quick connection between the output shaft 12 and the input shaft 22, and further achieving a quick connection between the handpiece body 1 and the treatment tip 2, thereby improving work efficiency.

The technical solution of the present application sets a first guiding element at the first end of the output shaft 12, and sets a second guiding element at the other end of the input shaft 22, and the first end is opposite to the other end. When the other end of the output shaft 12 is connected to the first end of the input shaft 22, by a connection and installation between the first guiding element and the second guiding element, the quick connection between the output shaft 12 and the input shaft 22 is realized. The driving shaft of the driving assembly 11 drives the output shaft 12 to rotate, and then drives the input shaft 22 to rotate, and finally drives the transducer assembly 21 to move, thus saving installation time, and improving work efficiency.

The connection and installation of the first guiding element and the second guiding element is any mechanical connection method, specifically including one or more of magnetic connection, threaded connection, sliding connection, bayonet connection, key connection, coupling, welding or any other known connection.

Specifically, in an embodiment, the first guiding element includes a plurality of bosses 121 protruding from the first end of the output shaft 12, the plurality of the bosses 121 are provided at intervals along a circumferential direction of the output shaft 12, and each of the bosses 121 is extending along a radial direction of the output shaft 12; one end of the boss 121 close to the treatment tip 2 is formed with two guide surfaces 122, and one end of the boss 121 away from the treatment tip 2 is formed with two first transmission inclined surfaces 123. The second guiding element includes a plurality of protrusions 221 provided at the opposite end of the input shaft 12, the plurality of the protrusions 221 are provided at intervals along a circumferential direction of the input shaft 22, and two adjacent protrusions are enclosed to form a receiving groove 221 for receiving the boss 121. Two guide convex edges 223 are formed at both sides of each protrusion 221, and two second transmission inclined surfaces 224 with an included angle are formed between the two second guide convex edges 223.

In this embodiment, a plurality of bosses 121 are protruding from the other end of the output shaft 12, one end of each boss 121 converges at the middle position of the output shaft 12, and the other end of each boss 121 is evenly distributed in the circumferential direction of the output shaft 12. The included angle between every two bosses 121 should be the same, and the plurality of bosses 121 are symmetrically distributed with the center of the output shaft 12 as the center. The number of bosses 121 should be more than three, and can be three, four or five, etc., which is not further limited here. Correspondingly, a plurality of protrusions 221 are protruding from the other end of the input shaft 22, and the plurality of protrusions 221 are evenly distributed along the circumferential direction of the input shaft 22, and the included angle between every two protrusions 221 should be identical, and the plurality of protrusions 221 are symmetrically distributed with the center of the input shaft 22 as the center, and the number of the protrusions 221 should be consistent with the number of the bosses 121, which can be three, four or five, etc. The plurality of protrusions 221 are enclosed to form a receiving groove 222, and the shape of the receiving groove 222 is the same as the shape formed by the combination of the plurality of bosses 121, and the plurality of bosses 121 are provided in the receiving groove 222, so that the output shaft 12 can drive the input shaft 22 to rotate together. Two guide surfaces 122 provided at an included angle are formed on both sides of the top surface of each boss 121. Correspondingly, two guide convex edges 223 provided at an included angle are formed on both sides of the top surface of each protrusion 221. The included angle between two guide convex edges 223 with a close distance between two adjacent protrusions 221 should be identical with the included angle between two guide surfaces 122 on the same boss 121, so that each boss 121 is inserted between two adjacent protrusions 221, thereby making the output shaft 12 drive the input shaft 22 to rotate together. The mutually coordinated structure of the boss 121 and the protrusion 221 as above can make the output shaft 12 and the input shaft 22 in any state be assembled into one body without manually adjusting the position of the output shaft 12 or the input shaft 22, thus saving time and improving efficiency. Two first transmission inclined surfaces 123 are further formed at one end of the boss 121 away from the treatment tip 2, and correspondingly, two second transmission inclined surfaces 224 with an included angle are formed between the two guide convex edges 223. After the output shaft 12 and the input shaft 22 are installed, one first transmission inclined surface 123 is abutted against one second transmission inclined surface 224, and the first transmission inclined surface 123 pushes the second transmission inclined surface 224, so that the output shaft 12 can drive the input shaft 22 to rotate together. Setting the first transmission inclined surface 123 and the second transmission inclined surface 224 can make the connection between the input shaft 22 and the output shaft 12 more stable, and the transmission effect better.

In an embodiment, a first chamfer 124 is provided between the two first transmission inclined surfaces 123 between two adjacent bosses 121; and a second chamfer 225 is provided between the two second transmission inclined surfaces 224 on a same protrusion 221, and the first chamfer 124 and the second chamfer 225 are connected in interference fit.

In order to further improve the transmission effect between the input shaft 22 and the output shaft 12, in this embodiment, a first chamfer 124 is provided between the two first transmission inclined surfaces 123 between the two adjacent bosses 121. Correspondingly, a second chamfer 225 is provided between the two second transmission inclined surfaces 224 on the same protrusion 221. When the output shaft 12 and the input shaft 22 are assembled and connected, the second chamfer 225 and the first chamfer 124 are connected in interference fit, so that the connection between the input shaft 22 and the output shaft 12 is tighter.

In an embodiment, an included angle between the two guide surfaces 122 on the same boss is 10° to 120°.

In this embodiment, the included angle between the two guide surfaces 122 on the same boss 121 is 10° to 120°, such as 10°, 20°, 30°, 40°, 50°, 60°, 70°, 80°, 90°, 100°, 110° or 120°, and certainly, it can also be any angle within the above range, and the present application does not make further restrictions on this. The larger the angle, the more difficult it is to assemble the treatment tip 2, but the more stable the connection. The smaller the angle, the easier it is to assemble the treatment tip 2, but the connection is unstable.

In an embodiment, the guide surface 122 includes an inclined surface or a curved surface.

In this embodiment, the guide surface 122 can be an inclined surface, which is a plane that can achieve pushing against the guide convex edge 223 to push the input shaft 22 to rotate. It is understandable that the guide surface 122 can also be a curved surface. By designing the curvature of the curved surface and the angle of the guide convex edge 223, the guide curved surface can also achieve pushing against the guide convex edge 223, thereby pushing the input shaft 22 to rotate.

In an embodiment, a first safety plane 125 is provided at an intersection of the two guide surfaces 122 on a same boss 121, and a width of the first safety plane 125 is in a range of 0.01 mm to 2 mm.

In this embodiment, in order to prevent the included angle at the intersection of the two guide surfaces 122 from being too sharp and causing injuries to the operator, a first safety plane 125 is provided at the intersection of the two guide surfaces 122 to soften the sharp angle and prevent injuries. The width of the first safety plane 125 is in a range of 0.01 mm to 2 mm, such as 0.01 mm, 0.08 mm, 0.4 mm, 1 mm, 1.5 mm, 2 mm, etc. Certainly, it can also be any value within the above range, and the present application does not make any further restrictions on this.

In an embodiment, each of the protrusions 221 is further provided with two cutting inclined surfaces 226 at an included angle, the guide convex edge 223 is provided at a connection between one of the cutting inclined surfaces 226 and one of the second transmission inclined surfaces 224, a second safety plane 227 is provided at a connection area between the two cutting inclined surfaces 226, and a width of the second safety plane 227 is 0.01 mm to 2 mm.

In this embodiment, two cutting inclined surfaces 226 at an included angle are formed on the protrusion 221, and the guide convex edge 223 is provided at the connection between one of the cutting inclined surfaces 226 and one of the second transmission inclined surfaces 224, which can be easily processed to form the guide convex edge 223 on the protrusion 221. A second safety plane 227 is provided at the connection area between the two cutting inclined surfaces 226 to soften the sharp angle and prevent the operator from being cut. The width of the second safety plane 227 is 0.01 mm to 2 mm, for example, 0.01 mm, 0.08 mm, 0.4 mm, 1 mm, 1.5 mm, 2 mm, etc. Certainly, it can also be any value within the above range, and the present application does not make any further limitation on this.

Figure 12:
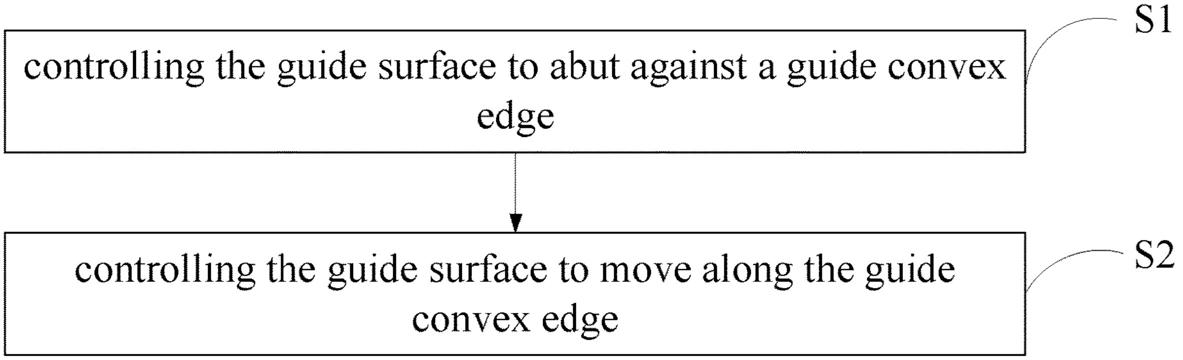
FIG. 12 is a schematic flow chart of an installation method of a treatment handpiece according to an embodiment of the present application.

The present application further proposes an installation method applied to the treatment handpiece 10 as described above, referring to FIG. 12, the installation method includes the following steps:

Step S1: controlling the guide surface 122 to abut against a guide convex edge 223.

Step S2: controlling the guide surface 122 to move along a length direction of the guide convex edge 223.

In this embodiment, firstly, controlling the guide surface 122 to abut against the guide convex edge 223 to play a preliminary guiding effect, resulting in preliminary connection between the output shaft 12 and the input shaft 22, and then controlling the guide surface 122 to move along the length direction of the guide convex edge 223, thereby realizing the movement of the output shaft 12 relative to the input shaft 22, realizing the quick connection between the output shaft 12 and the input shaft 22, and improving the work efficiency.

In an embodiment, the guide surface 122 includes a plurality of bosses protruding from the first end, the plurality of the bosses are provided at intervals along a circumferential direction of the output shaft 12, and each of the bosses is extended along a radial direction of the output shaft 12; one end of the boss close to the treatment tip 2 is formed with two guide surfaces. The guide convex edge 223 includes a plurality of protrusions provided at the other end of the input shaft 12, the plurality of the protrusions are provided at intervals along a circumferential direction of the input shaft 12, and two adjacent protrusions are enclosed to form a receiving groove for receiving the boss; two guide convex edges 223 are formed on both sides of each protrusion. The installation method includes the following steps:

controlling the guide surface to abut against a guide convex edge 223; and controlling the guide surface to move along a length direction of the guide convex edge 223.

Figure 13:
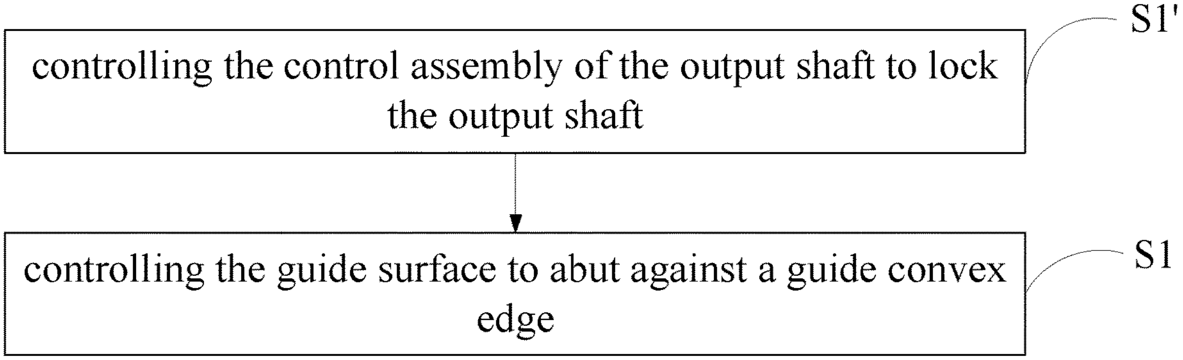
FIG. 13 is a schematic flow chart of an installation method of a treatment handpiece according to an embodiment of the present application.

In an embodiment, referring to FIG. 13, the treatment handpiece 10 further includes a control assembly of the output shaft 12, and before the controlling the guide surface 122 to abut against the guide convex edge 223, further including:

Step S1': controlling the control assembly of the output shaft 12 to lock the output shaft 12.

In this embodiment, the end of the treatment handpiece 10 is further provided with a control assembly of the output shaft 12, and before controlling the guide surface 122 to abut against a guide convex edge 223, controlling the control assembly of the output shaft 12 to lock the output shaft 12, so that the output shaft 12 cannot rotate, and the output shaft 12 is prevented from being pushed by the input shaft 22 and causing dislocation, thereby causing connection failure. The control assembly of the output shaft 12 can be a combination of a shaft sleeve and a photoelectric sensor. One end of the shaft sleeve is sleeved on the driving shaft of the driving assembly 11, and the other end of the shaft sleeve is connected to the output shaft 12. The outer peripheral wall of the shaft sleeve is provided with a baffle piece. The baffle piece has two states: blocking the optical path of the photoelectric sensor and avoiding the optical path of the photoelectric sensor. The output shaft 12 is set beforehand to be in the correction state when the optical path of the photoelectric sensor is blocked. Once the photoelectric sensor cannot detect the optical signal, it means that the output shaft 12 is in the initial state at this time. At this time, the photoelectric sensor controls the driving assembly 11 to lock the driving shaft, and then locks the output shaft 12, and directly assembles and connects the output shaft 12 with the input shaft 22. It should be noted that the control assembly of the output shaft 12 can also be other devices, such as an angle sensor, which determines and controls whether the output shaft 12 is in the initial state by detecting the angle change of the output shaft 12.

Figure 14:
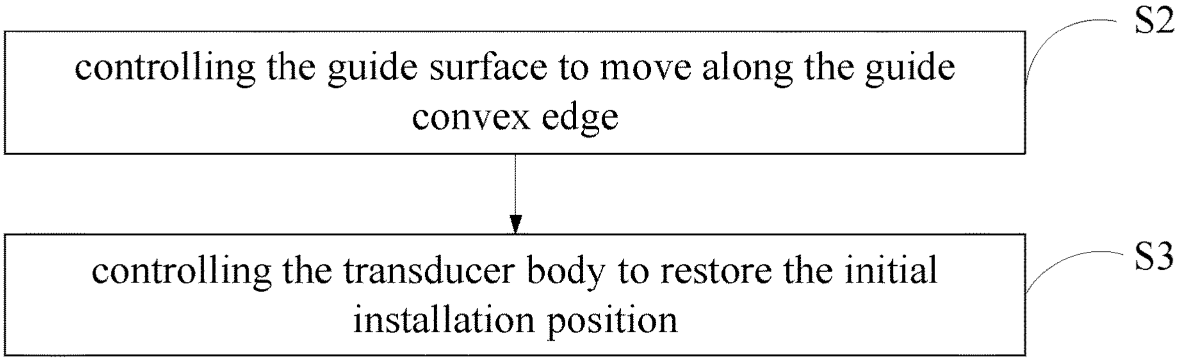
FIG. 14 is a schematic flow chart of an installation method of a treatment handpiece according to an embodiment of the present application.

In an embodiment, referring to FIG. 14, the transducer assembly 21 includes a transducer motion assembly 19 and a transducer body 212, the transducer motion assembly 19 is connected to one end of the input shaft 22 and is configured to convert a rotary motion of the input shaft 22 into a linear reciprocating motion of the transducer body 212, and the transducer body 212 is provided with an initial installation position. After the controlling the guide surface 122 to move along the length direction of the guide convex edge 223, the method further including:

Step S3: controlling the transducer body 212 to restore the initial installation position.

In this embodiment, the transducer assembly 21 includes a transducer motion assembly 19 and a transducer body 212. The rotary motion part 211 is connected to the input shaft 22, and can convert the circumferential rotation of the input shaft 22 into a linear reciprocating motion, thereby driving the transducer body 212 to perform linear reciprocating motion. The transducer motion assembly 19 can be a crank slider mechanism, or a combination of a gear wheel with missing teeth and a gear rack, and the present application does not make further limitations here. When the locked output shaft 12 is connected to the input shaft 22, the first inclined surface can push against the second inclined surface, thereby driving the input shaft 22 to rotate, so that the input shaft 22 also rotates to the correction state, thereby driving the transducer motion assembly 19 and the transducer body 212 to move together, until the transducer body 212 returns to the bottom of the input shaft 22 and returns to the initial position, so as to facilitate the next treatment.

Figure 7:
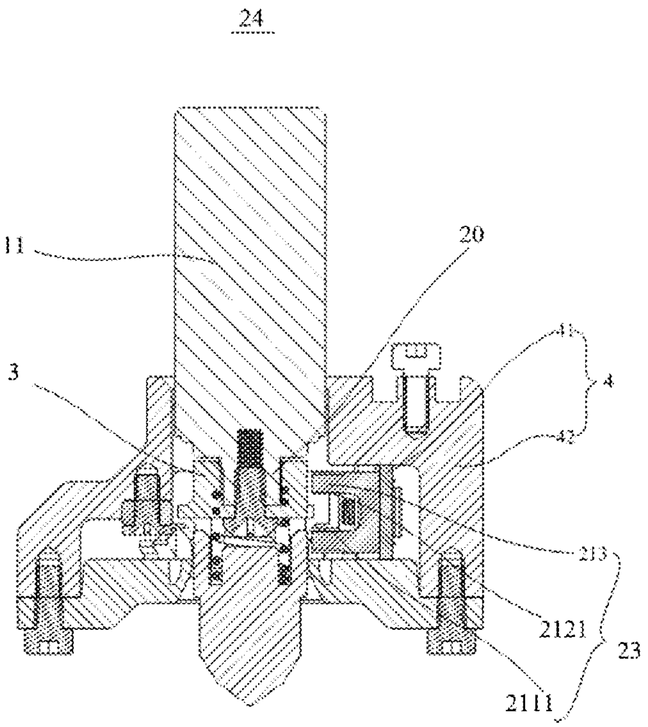
FIG. 7 is a structural schematic view of a treatment handpiece according to an embodiment of the present application.
Figure 8:
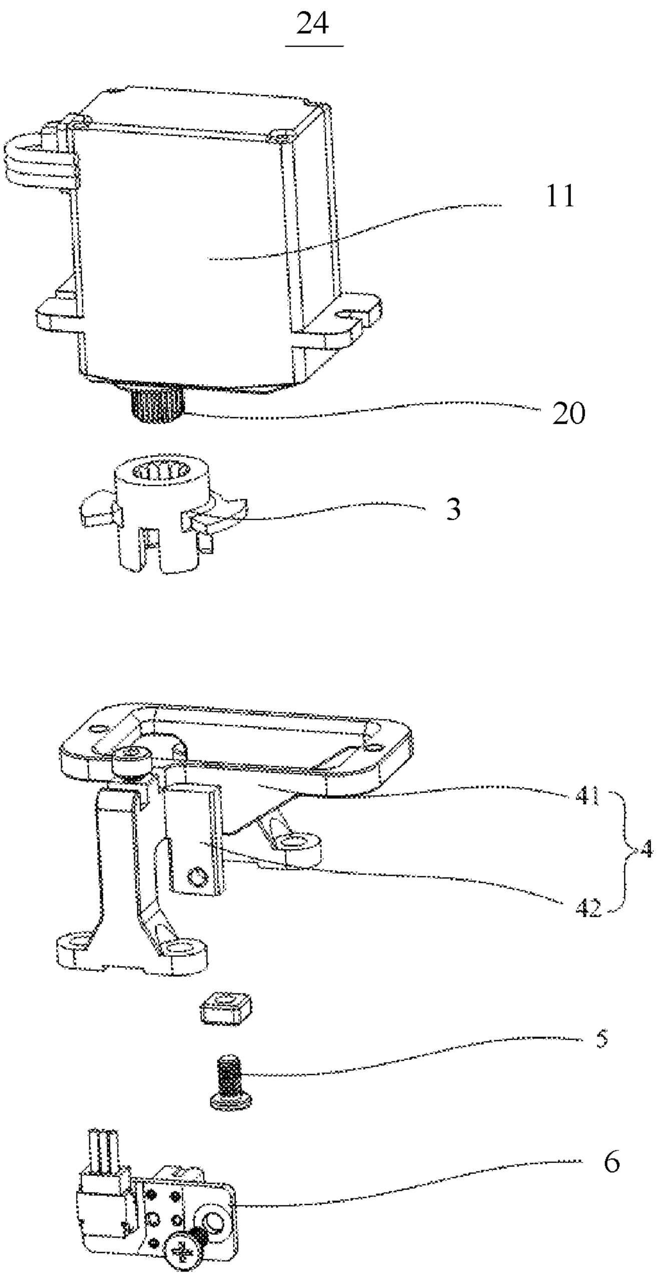
FIG. 8 is an exploded view of a treatment handpiece according to an embodiment of the present application.
Figure 9:
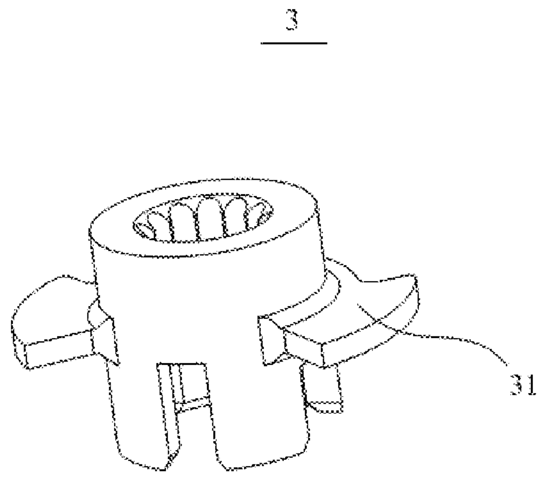
FIG. 9 is a structural schematic view of a shaft sleeve in FIG. 8.

The present application further proposes a treatment handpiece 10, combined with reference to FIG. 7 to FIG. 9, which includes a handpiece body 24 and a treatment tip (not shown in figure). The handpiece body 24 includes a driving assembly 11 and a sensor assembly 6. The sensor assembly 6 is electrically connected to the driving assembly 11 to detect and control a rotation angle of a driving shaft 20 of the driving assembly 11. The driving shaft 20 is provided with a preset correction position. The treatment tip includes an input shaft and a transducer assembly 21. One end of the input shaft is connected to the driving shaft 20, and the other end of the input shaft is connected to the transducer assembly 21. The driving shaft 20 is configured to drive the input shaft while the input shaft 21 drives the transducer assembly to move linearly.

In this embodiment, a sensor assembly 6 is provided at a handpiece body 24 of a treatment handpiece 10 for detecting a position state of a driving shaft 20 of a driving assembly 11 and being electrically connected to the driving assembly 11, automatically controlling the driving shaft 20 of the driving assembly 11 to rotate to a specified position, stopping and locking the driving shaft 20 in time, thereby aligning and connecting with an input shaft of the treatment tip, without the need for repeated multiple manual calibration, thereby saving manpower and time costs. The sensor assembly 6 can adopt a Hall sensor disposed on the outer peripheral wall of the driving shaft 20, determining whether the position of the driving shaft 20 is corrected by measuring the rotation angle of the driving shaft 20. A photoelectric sensor can also be adopted to set a circle of convex plates with notches on the outer peripheral wall of the driving shaft 20. The convex plates block the optical signal reception of the photoelectric sensor. The correction position of the driving shaft 20 is set so that when the photoelectric sensor receives the optical signal, the driving shaft 20 is in the correction position, and the automatic correction of the driving shaft 20 can also be achieved, and the present application does not make further restrictions here. The driving assembly 11 is a common motor assembly on the market. The model and specification should be specifically selected according to the specifications and speed requirements of the treatment handpiece 10, and the present application does not make further restrictions on this.

The technical solution of the present application adopts a sensor assembly 6 to detect the rotation angle state of the driving shaft 20 of the driving assembly 11, and is electrically connected to the driving assembly 11, so as to control the driving shaft 20 of the driving assembly 11 to rotate or stop in time, thereby realizing the automatic correction of the driving shaft 20 of the handpiece body 24, and being able to lock the driving shaft 20 after the driving shaft 20 rotates to the correction position, thereby realizing the rapid installation of the handpiece body 24 and the treatment tip, and saving manpower and time costs.

In an embodiment, the handpiece body 24 further includes a first limit part 5, and the first limit part 5 is configured to limit the rotation angle of the driving shaft 20.

In this embodiment, a first limit part 5 is provided at the handpiece body to limit the rotation angle of the driving shaft 20. When the driving shaft 20 abuts against the first limit part 5 and cannot continue to rotate, the rotation position of the driving shaft 20 is set as the correction position. Subsequently, the driving shaft 20 of the driving assembly 11 only needs to be controlled by the sensor assembly 6 to rotate until the driving shaft 20 abuts against the first limit part 5, which can save the detecting step of the current rotation angle of the driving shaft 20, thus further improving the speed of correcting the driving shaft 20, and then quickly connecting the handpiece body 24 and the treatment tip, and saving manpower and time costs.

In an embodiment, the transducer assembly 21 includes a transducer motion assembly 21 and a transducer body 212, and a side of the transducer motion assembly 21 is connected to the other end of the input shaft and the opposite side of the transducer motion assembly is connected to the transducer body such that a rotary motion of the input shaft is converted into a linear reciprocating motion of the transducer body.

In this embodiment, the transducer assembly 21 includes a transducer motion assembly 21 and a transducer body 212. The transducer motion assembly 21 is connected to the other end of the input shaft, and can convert the circumferential rotation of the input shaft into the linear reciprocating motion, thereby driving the transducer body 212 to perform the linear reciprocating motion, thus achieving a planar treatment effect. The transducer motion assembly 21 can be a crank slider mechanism, or can be a combination of a gear wheel with missing teeth and a gear rack, which is not further limited in the present application.

In an embodiment, the transducer body 212 is provided with a preset position; in response to that the driving shaft 20 being in the correction position is connected to the input shaft, the transducer body 212 returns to the preset position.

In this embodiment, in order to facilitate subsequent treatment, the transducer body 212 is set with a preset position. The preset position can be the middle position of the treatment tip, or one side of the treatment tip, or any position, which is not further limited in the present application. When the driving shaft 20 being in the correction position is connected to the input shaft, the driving shaft 20 is locked, driving the input shaft to rotate, thereby driving the transducer motion assembly 21 to move, and then driving the transducer body 212 to move, causing it to return to the preset position.

In an embodiment, the treatment tip further includes a second limit part, and the second limit part is configured to limit a displacement distance of the transducer body 212.

In this embodiment, the second limit part is set on the treatment tip, and the second limit part is configured to limit the displacement distance of the transducer body 212, thus preventing excessive displacement of the transducer body 212 and causing a stuck phenomenon.

As shown in FIG. 7 to FIG. 9, in an embodiment, the handpiece body 24 further includes a shaft sleeve 3, one end of the shaft sleeve 3 is sleeved on the driving shaft 20, and a shielding part 31 is provided at an outer peripheral wall of the shaft sleeve 3. The sensor assembly 6 is a photoelectric sensor assembly 332, the photoelectric sensor assembly 332 is provided close to the shaft sleeve 3, and the shielding part 31 is provided with a first state of blocking an optical signal of the photoelectric sensor assembly 332 and a second state of avoiding the optical signal of the photoelectric sensor assembly 332.

In this embodiment, a photoelectric sensor assembly 332 is adopted as a sensor assembly 6 for detecting the position state of a driving shaft 20. Meanwhile, a shaft sleeve 3 is sleeved on the outer periphery of the driving shaft 20. The shaft sleeve 3 can rotate together with the driving shaft 20. A shielding part 31 is provided at the outer peripheral wall of the shaft sleeve 3. When the shielding part 31 is in the first state, it can block the reception of an optical signal of the photoelectric sensor. When the shielding part 31 is in the second state, it avoids the optical signal of the photoelectric sensor. The position of the shaft sleeve 3 is preset. When the shielding part 31 is in the first state, the position of the driving shaft 20 is defined as the correction position. When the position of the driving shaft 20 needs to be calibrated, the photoelectric sensor determines whether the optical signal is received. If the optical signal is received, it means that the shielding part 31 is in the second state, the position of the driving shaft 20 is not the correction position, and the driving assembly 11 is controlled to drive the driving shaft 20 to rotate until the photoelectric sensor does not receive the optical signal. If the optical signal is not received, it means that the shielding part 31 is in the first state, and the position of the driving shaft 20 is in the correction position, and no correction is required. The material of the shaft sleeve 3 can be metal, such as stainless steel or titanium alloy, or engineering plastic, which is not further limited here. It can be understood that, under the premise of being able to block the optical signal, the shorter the length of the shielding part 31, the more accurate the position correction of the driving shaft 20, the specific length should be self-selected according to actual needs, and the present application does not make further restrictions on this.

In an embodiment, combined with reference to FIG. 9, two shielding parts 31 are provided, and the two shielding parts 31 are symmetrically provided at the outer peripheral wall of the shaft sleeve 3.

In this embodiment, since the driving shaft 20 is generally a cylindrical structure, and the structure at the end is a centrally symmetrical structure, the correction position of the driving shaft 20 is not unique. Therefore, symmetrically setting two shielding parts 31 on the outer peripheral wall of the shaft sleeve 3 can shorten the time required for correcting the driving shaft 20, further saving time cost, and improving efficiency.

Please refer to FIG. 7 and FIG. 8, in an embodiment, the handpiece body 24 further includes a shell and a bracket 4. The shell is provided with a receiving cavity and is provided with an avoiding hole for the driving shaft 20 to pass through, the bracket 4 is provided at the receiving cavity, and the driving assembly 11 is provided at the receiving cavity and provided at the bracket 4.

In this embodiment, the handpiece body 24 further includes a shell and a bracket 4. The shell has a receiving cavity, and an avoidance hole is provided on the shell. The bracket 4, the driving assembly 11 and the sensor assembly 6 are all provided in the receiving cavity and protected by the shell, thus playing the role of waterproof and dust-proof. The bracket 4 is connected to the shell on one side and connected to the driving assembly 11 on the other side, playing the role of stably supporting the driving assembly 11. The driving shaft 20 passes through the avoidance hole of the shell and is connected to the input shaft of the treatment tip, thus realizing the power output of the driving assembly 11 to the treatment tip. The shell and the bracket 4 can be made of metal materials, such as aluminum alloy or titanium alloy, or can adopt hard engineering plastic materials, which are not further limited here.

In an embodiment, combined with reference to FIG. 7 and FIG. 8, the bracket 4 includes a base 41 for fixing the driving assembly 11 and a baffle plate 42 connected to the base 41, and the baffle plate 42 is parallel to an axial direction of the shaft sleeve 3. The photoelectric sensor assembly 332 includes two supporting arms 213 opposite to each other, a transmitting part 2111 and a receiving part 2121, the two supporting arms 213 are provided at intervals at the baffle plate 42, and the transmitting part 2111 and the receiving part 2121 are opposite to each other at the two supporting arms 213. In response to that the shielding part 31 is in the first state, the shielding part 31 is provided between the transmitting part 2111 and the receiving part 2121.

In this embodiment, the bracket 4 includes a base 41 and a baffle plate 42. The base 41 is configured to install the driving assembly 11. The baffle plate 42 is parallel to the axial direction of the shaft sleeve 3, and is configured to install the photoelectric sensor assembly 332. The photoelectric sensor assembly 332 includes a beam supporting arm 213, a transmitting part 2111 and a receiving part 2121, the two supporting arms 213 are provided on the baffle plate 42 at an interval and toward the direction of the shaft sleeve 3, the transmitting part 2111 and the receiving part 2121 are also respectively provided at the opposite position of the two supporting arms 213, thus realizing the transmission and reception of the optical signal. When the shielding part 31 is in the first state, it can be located between the transmitting part 2111 and the receiving part 2121, thus blocking the reception of the optical signal, helping to determine the position state of the driving shaft 20, so as to correct the driving shaft 20.

The present application further proposes an ultrasonic therapeutic apparatus, which includes a treatment handpiece 10. The specific structure of the treatment handpiece 10 refers to the above embodiment. Since the ultrasonic therapeutic apparatus adopts all the technical solutions of all the above embodiments, it has at least all the beneficial effects brought by the technical solutions of the above embodiments, which will not be repeated here.

Figure 10:
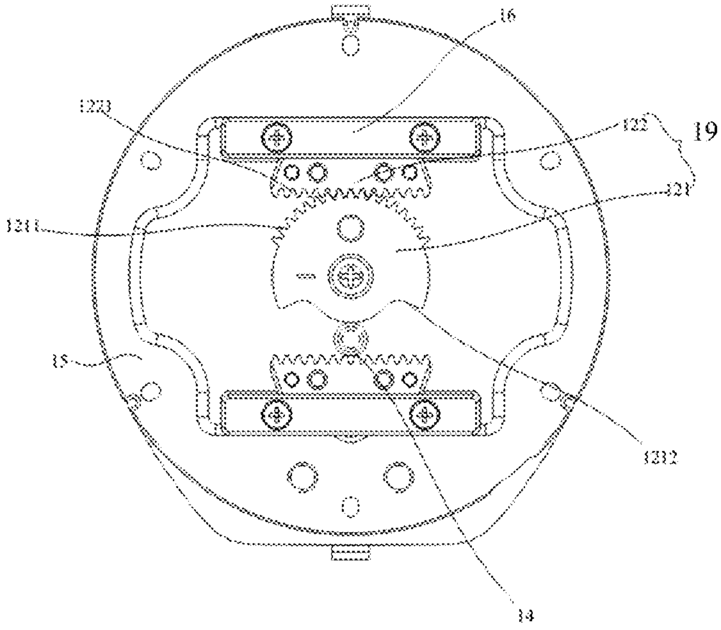
FIG. 10 is a structural schematic view of a treatment tip according to an embodiment of the present application.
Figure 11:
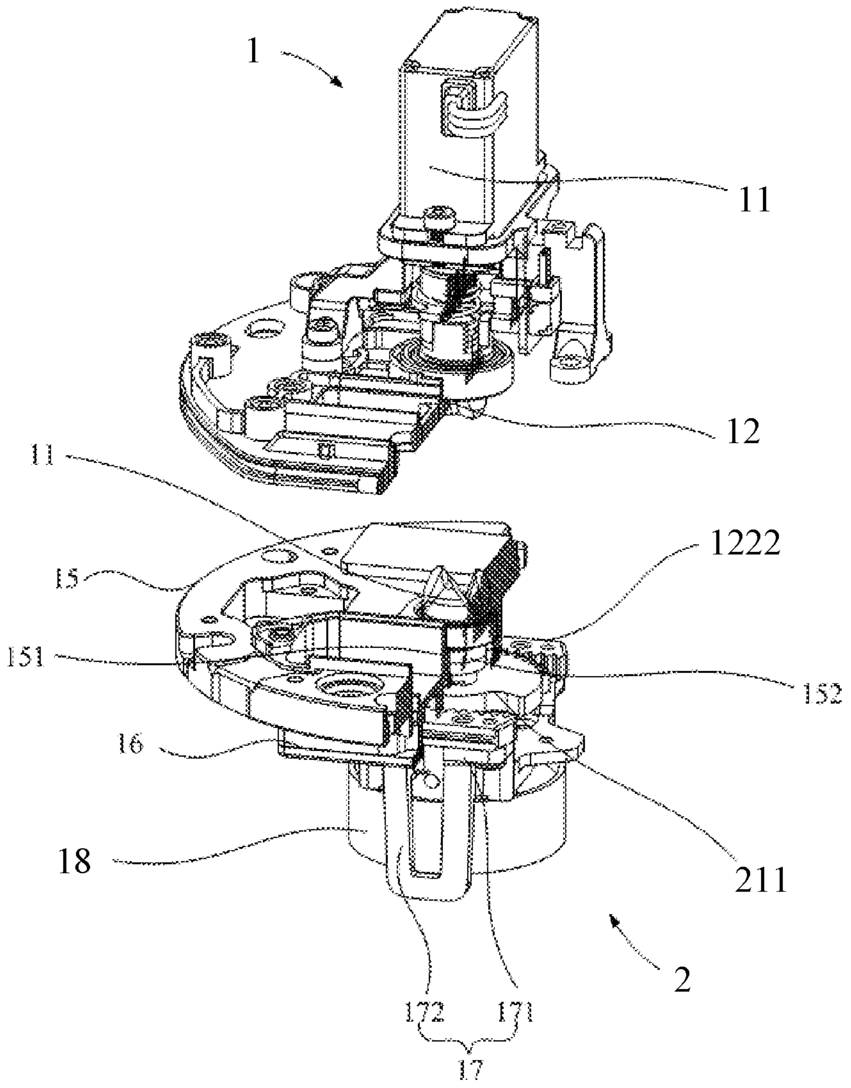
FIG. 11 is a structural schematic view of a treatment handpiece according to an embodiment of the present application.

An embodiment of the present application proposes a treatment tip 2, combined with reference to FIG. 10 and FIG. 11, the treatment tip 2 includes an input shaft 22, a transducer motion assembly 19 and a transducer 18 (which is the identical with the transducer body 212 in the aforementioned embodiment). One end of the input shaft 22 is connected to the output shaft 12 of the driving assembly 11. The transducer motion assembly 19 includes a rotary motion part 211 and a linear motion part 1222. The rotary motion part 211 is drivingly connected to the other end of the input shaft 22 away from the output shaft 12. The linear motion part 1222 is drivingly connected to the rotary motion part 211. The transducer 18 is connected to the linear motion part 1222. The input shaft 22 drives the rotary motion part 211 to rotate while the rotary motion part 211 drives the linear motion part 1222 to linearly move, such that the transducer 18 moves linearly.

In this embodiment, the input shaft 22 is configured to transmit the driving force of the output shaft 12 from the driving assembly 11, and one end is connected to the output shaft 12. The connection method of the input shaft 22 and the output shaft 12 can adopt a connection method of direct connection because the rotation speed is relatively low, and can also adopt other connection methods such as couplings or key connections. The present application does not make further restrictions on this, as long as the input shaft 22 can rotate with the output shaft 12. The transducer motion assembly 19 includes a rotary motion part 211 and a linear motion part 2122. The rotary motion part 211 is connected to the other end of the input shaft 22. The connection method between the rotary motion part 211 and the input shaft 22 can be a screw connection, or can be a clamping connection or welding, etc. As long as the rotary motion part 211 can rotate together with the input shaft 22, the present application does not make any further limitations on this.

The rotary motion part 211 drives and connects the linear motion part 1222, and can convert the rotary motion of the rotary motion part 211 into the linear motion of the linear motion part 1222, thereby driving the transducer 18 connected to the linear motion part 1222 to perform linear reciprocating motion. It should be noted that the combination of the rotary motion part 211 and the linear motion part 1222 can be a crank slider structure, the crank and the slider are connected, and a slide groove is provided to limit the motion trajectory of the slider to make it a straight line. The input shaft 22 drives the crank to rotate together and then drives the slider to perform linear reciprocating motion along the slide groove, thereby driving the transducer 18 to perform linear reciprocating motion.

In an embodiment, the combination of the rotary motion part 211 and the linear motion part 1222 can further be a combination of a gear wheel with missing teeth and a gear rack. The two gear racks are symmetrically provided at both sides of the gear wheel with missing teeth. The two gear racks can move together. The gear wheel with missing teeth rotates solely towards one direction driven by the input shaft 22. When the tooth part of the gear wheel with missing teeth meshes with the tooth part of one of the gear racks, the gear rack moves along the tangent direction of the rotation direction of the gear wheel with missing teeth. When the tooth part of the gear wheel with missing teeth rotates to the other side, it meshes with the tooth part of the other gear rack, driving the gear rack to move along the tangent direction of the rotation direction of the gear wheel with missing teeth. Since the rotation directions of the gear wheel with missing teeth on both sides are opposite, the linear reciprocating motion of the gear rack can be realized.

In an embodiment, the combination of the rotary motion part 211 and the linear motion part 1222 can further be a combination of a gear wheel and a gear rack. In this case, the input shaft 22 should have a periodic bidirectional rotary motion state, the tooth part of the gear wheel is meshed and connected with the tooth part of the gear rack, the input shaft 22 drives the gear wheel to perform periodic bidirectional rotary motion, and then drives the gear rack and the transducer 18 connected thereto to perform linear reciprocating motion. The combination of the rotary motion part 211 and the linear motion part 1222 is not unique, as long as the rotary motion of the input shaft 22 can be converted into the linear reciprocating motion of the transducer 18, and no further limitation is made here.

The treatment tip 2 proposed in the technical solution of the present application includes an input shaft 22, a transducer motion assembly 19 and a transducer 18. The transducer motion assembly 19 further includes a rotary motion part 211 and a linear motion part 1222. The output shaft 12 of the driving assembly 11 is connected to the input shaft 22, and the power of the driving assembly 11 is transmitted to the input shaft 22 of the treatment tip 2. The input shaft 22 then drives and connects the rotary motion part 211 to rotate, and finally drives the linear motion part 1222, thus converting the rotary motion of the input shaft 22 into a linear reciprocating motion of the linear motion part 1222. The transducer 18 is connected to the linear motion part 1222, so as to perform linear reciprocating motion with the linear motion part 1222, thereby realizing the planar treatment of the treatment tip 2, and saving manpower. The treatment tip 2 proposed in the present application realizes the lateral movement of the transducer 18 by the combination of the rotary motion part 211 and the linear motion part 1222, with a simple and compact structure and high transmission efficiency.

Please refer to FIG. 11, in an embodiment, the input shaft 22 is configured to drive the rotary motion part 211 to perform bidirectional reciprocating rotating motion, a side of the rotary motion part 211 facing the linear motion part 1222 is provided with a plurality of first tooth parts 1211, and a side of the linear motion part 1222 facing the rotary motion part 211 is provided with a plurality of second tooth parts 1221; the plurality of the first tooth parts 1211 are meshed and connected with the plurality of the second tooth parts 1221 to drive the linear motion part 1222 to perform linear reciprocating motion.

In this embodiment, the output shaft 12 of the driving assembly 11 has a motion state of periodic bidirectional rotation. A plurality of first tooth parts 1211 are partially provided at one side of the rotary motion part 211. A plurality of second tooth parts 1221 meshingly connected with the first tooth parts 1211 are provided at one side of the linear motion part 1222 facing the rotary motion part 211. By the meshing of the first tooth parts 1211 and the second tooth parts 1221, the rotary motion part 211 drives the linear motion part 1222 to move along the rotation tangent direction of the rotary motion part 211. Since the rotary motion part 211 performs periodic bidirectional rotary motion together under the drive of the input shaft 22, the linear motion part 1222 and the transducer 18 connected to the linear motion part 1222 performs horizontal linear reciprocating motion under the drive of the rotary motion part 211, thus achieving planar scanning treatment, and the tooth part meshing transmission mode has high transmission efficiency. Specifically, the length of the first tooth part 1211, the length of the second tooth part 1221 and the specific parameters of the tooth part, such as the number of tooth parts or the modulus of the tooth part, should be self-selected according to specific needs, and the present application does not make further restrictions on this. Materials of the linear motion part 1222 and the rotary motion part 211 can be engineering plastics, which are lightweight and have certain self-lubricating properties, or can be metal materials, such as stainless steel or aluminum alloy, which are strong and wear-resistant, and the present application does not make further restrictions on this.

Please refer to FIG. 11 again, in an embodiment, the opposite side of the rotary motion part 211 away from the first tooth part 1211 is provided with a limit groove 1212 extending along a circumferential direction; the treatment tip 2 further includes a limit part 14. One end of the limit part 14 is provided at the transducer 18, and the opposite end of the limit part is exposed at the limit groove 1212 to limit a rotation angle of the rotary motion part 211.

In this embodiment, a limit groove 1212 is provided at the opposite side of the rotary motion part 211 away from the first tooth part 1211, and the limit groove 1212 extends along the circumferential direction of the rotary motion part 211. At the same time, a limit part 14 is further provided, and the limit part 14 is provided in the limit groove 1212 to limit the rotation angle of the rotary motion part 211, so as to prevent the moving distance of the linear motion part 1222 from being too long due to the rotation angle of the rotary motion part 211 being too large, thereby colliding with the housing or other components and damaging the device. Specifically, the length of the limit groove 1212 and the installation position of the limit part 14 should be determined by oneself according to actual needs, and the present application does not make any further restrictions here. It can be understood that in other embodiments, the rotation angle and rotation period of the rotary motion part 211 can be controlled by adjusting and controlling the rotation speed and rotation period of the driving assembly 11, thereby controlling the moving distance and reciprocating frequency of the linear motion part 1222.

In an embodiment, in combination with FIG. 11, two linear motion parts 1222 are provided, and the two linear motion parts 1222 are symmetrically provided at two sides of the rotary motion part 211; two sides of the transducer 18 are respectively connected to the two linear motion parts 1222.

In this embodiment, two linear motion parts 1222 are symmetrically provided at two sides of the rotary motion part 211, and the two sides of the transducer 18 are respectively connected to two linear motion parts 1222, the connection between the transducer 18 and the linear motion part 1222 is more stable, and the motion of the transducer 18 is more stable. It can be understood that in other embodiments, due to the setting of the limit part 14 and the limit groove 1212, the rotary motion part 211 is only meshed and connected with one side of the linear motion part 1222, so a connection strip without a tooth part can be provided at the other side of the rotary motion part 211, which can also achieve the effect that connection is more stable and motion of the transducer 18 is more stable.

In an embodiment, combined with reference to FIG. 11, the output shaft 12 is configured to drive a rotational motion of the rotary motion part 211 solely towards one direction, and a side of the rotary motion part 211 facing the linear motion part 1222 is partially provided at a plurality of third tooth parts. Two linear motion parts 1222 are provided, and the two linear motion parts 1222 are symmetrically provided at both sides of the rotary motion part 211. A side of the two linear motion parts facing the rotary motion part is provided with a plurality of fourth tooth parts, and the plurality of the third tooth parts are meshed and connected with the plurality of the fourth tooth parts to drive the two linear motion parts 1222 to perform linear reciprocating motion.

In this embodiment, the output shaft 12 of the driving assembly 11 rotates solely towards one direction, driving the input shaft 22 of the treatment tip 2 to rotate solely towards one direction, thereby driving the rotary motion part 211 to rotate solely towards one direction. The two linear motion parts 1222 are symmetrically provided at both sides of the rotary motion part 211. The rotary motion part 211 rotates solely towards one direction. The third tooth parts of the rotary motion part 211 are first meshed and connected with the fourth tooth parts of the linear motion part 1222 on one side, driving the two linear motion parts 1222 to perform linear motion along the tangential direction of the rotation of the rotary motion part 211. When the rotary motion part 211 rotates to the other side and meshed and connected with the fourth tooth part of the linear motion part 1222 on the other side, the two linear motion parts 1222 are then driven to perform linear motion in the opposite direction to the previous direction along the tangent direction of the rotation of the rotary motion part 211, and then repeat the above process, so as to make the transducer 18 perform reciprocating linear motion, thus achieving the planar treatment effect of the treatment tip 2, and the transmission mode of the tooth part meshing has high transmission efficiency. Specifically, the length of the third tooth part, the length of the fourth tooth part and the specific parameters of the tooth part, such as the number of tooth parts or the modulus of the tooth part, should be self-selected according to specific needs, and the present application does not make further restrictions on this. Materials of the linear motion part 1222 and the rotary motion part 211 of this embodiment can be engineering plastics, which are light in weight and have certain self-lubricating properties, or can be metal materials, such as stainless steel or aluminum alloy, which are strong and wear-resistant, and the present application does not make further restrictions on this.

Please refer to FIG. 10, in an embodiment, the treatment tip 2 further includes a transducer bracket 17. The transducer bracket 17 includes a fixing part 171 and a clamping part 172. The fixing part 171 is configured to connect with the linear motion part 1222. The clamping part 172 is connected with the opposite side of the fixing part 171 away from the linear motion part 1222. The clamping part 172 is configured to clamp the transducer 18.

In this embodiment, a transducer bracket 17 is provided for connecting the linear motion part 1222 and the transducer 18, and can stably connect the transducer 18. The transducer bracket 17 includes a fixing part 171 and a clamping part 172. The fixing part 171 is configured to connect with the linear motion part 1222. The clamping part 172 is connected to the side of the fixing part 171 away from the linear motion part 1222. The connection method can adopt screw connection or welding connection, which is not further limited here. The clamping part 172 is configured to clamp the transducer 18, and compared with other connection methods, it is convenient to disassemble and replace the transducer 18.

In an embodiment, combined with reference to FIG. 10, the treatment tip 2 further includes an installation seat 15, an avoidance hole 151 is provided in a middle of the installation seat 15, the input shaft 22 passes through the avoidance hole 151 to be connected with the output shaft 12, and a sealing element 152 is provided between the input shaft 22 and the installation seat 15.

In this embodiment, the treatment tip 2 is provided with an installation seat 15, and the installation seat 15 is provided with an avoidance hole 151 for the input shaft to pass through, so as to be driven by the output shaft 12 to perform rotary motion, and then the input shaft 22 drives the rotary motion part 211 and the linear motion part 1222 to convert the rotary motion of the output shaft 12 into the lateral reciprocating motion of the transducer 18, thereby realizing the planar treatment of the treatment tip 2. Since the transducer 18 needs to use a sound-conducting medium to help transmit ultrasonic waves during the operation of the transducer 18, a sealing element 152 needs to be provided between the input shaft 22 and the installation seat 15 to seal the treatment tip 2 to prevent leakage of the sound-conducting medium and affect the working effect of the transducer 18. The sealing element 152 can adopt a sealing ring or a sealing strip, or even a sealing method such as glue, and the present application does not make further requirements for this. The installation seat 15 can adopt hard plastic, or can adopt metal, such as aluminum alloy, and no further restrictions are made here.

In an embodiment, combined with reference to FIG. 10 and FIG. 11, the treatment tip 2 further includes a guide track 16, the guide track 16 is provided at a surface of the installation seat 15 away from the output shaft 12, and the other side of the linear motion part 1222 away from the rotary motion part 211 is slidably connected to the guide track 16 to perform linear motion along an extension direction of the guide track 16.

In order to control the motion trajectory of the linear motion part 1222, and further control the motion trajectory of the transducer 18, in this embodiment, the guide track 16 is provided at the surface of the installation seat 15 away from the driving shaft, and the guide track 16 is slidably connected to the other side of the linear motion part 1222 away from the rotary motion part 211, so that the linear motion part 1222 can only perform linear reciprocating motion along the guide track 16. It should be noted that a convex strip may be provided on the guide track 16, a groove may be provided at the other side of the linear motion part 1222 away from the rotary motion part 211, and the convex strip may be slidably provided in the groove, so that the linear motion part 1222 may perform linear motion along the guide track 16. A groove may also be provided on the guide track 16, a convex strip may be provided at the other side of the linear motion part 1222 away from the rotary motion part 211, and the convex strip may be slidably provided in the groove, so that the linear motion part 1222 may perform linear motion along the guide track 16, and the present application does not make further limitations here.

The present application further proposes a treatment handpiece, the treatment handpiece includes a handpiece body 1 and a treatment tip 2. The specific structure of the treatment tip 2 refers to the above embodiment. Since this treatment handpiece adopts all the technical solutions of all the above embodiments, it at least has all the beneficial effects brought by the technical solutions of the above embodiments, which will not be repeated here. The handpiece body 1 includes the driving assembly 11, and the treatment tip 2 is the treatment tip 2 described in any of the above embodiments. The output shaft 12 of the driving assembly 11 is configured to drive and connect an input shaft 22 of the treatment tip 2.

In this embodiment, the treatment handpiece includes a handpiece body 1 and a treatment tip 2. A driving assembly 11 is provided in the handpiece body 1. The driving assembly 11 has a rotatable output shaft 22, such as a motor. By providing a first guiding element at a first end of the output shaft 22 and providing a second guiding element at the other end of an input shaft 22 of the treatment tip 2, realizing a driving connection of the output shaft 12 of the driving assembly 11, and driving the input shaft 22 of the treatment tip 2 to rotate, so as to transmit the driving force of the driving assembly 11 to the input shaft 22 of the treatment tip 2, thereby driving the transducer motion assembly 19 and the transducer 18 to perform linear motion. The connection and installation of the first guiding element of the output shaft 12 and the second guiding element of the input shaft 22 is any mechanical connection method, specifically including one or more of magnetic connection, threaded connection, sliding connection, bayonet connection, key connection, coupling, welding or any other known connection, or further can be a direct connection, which is not further limited in the present application.

Figure 15:
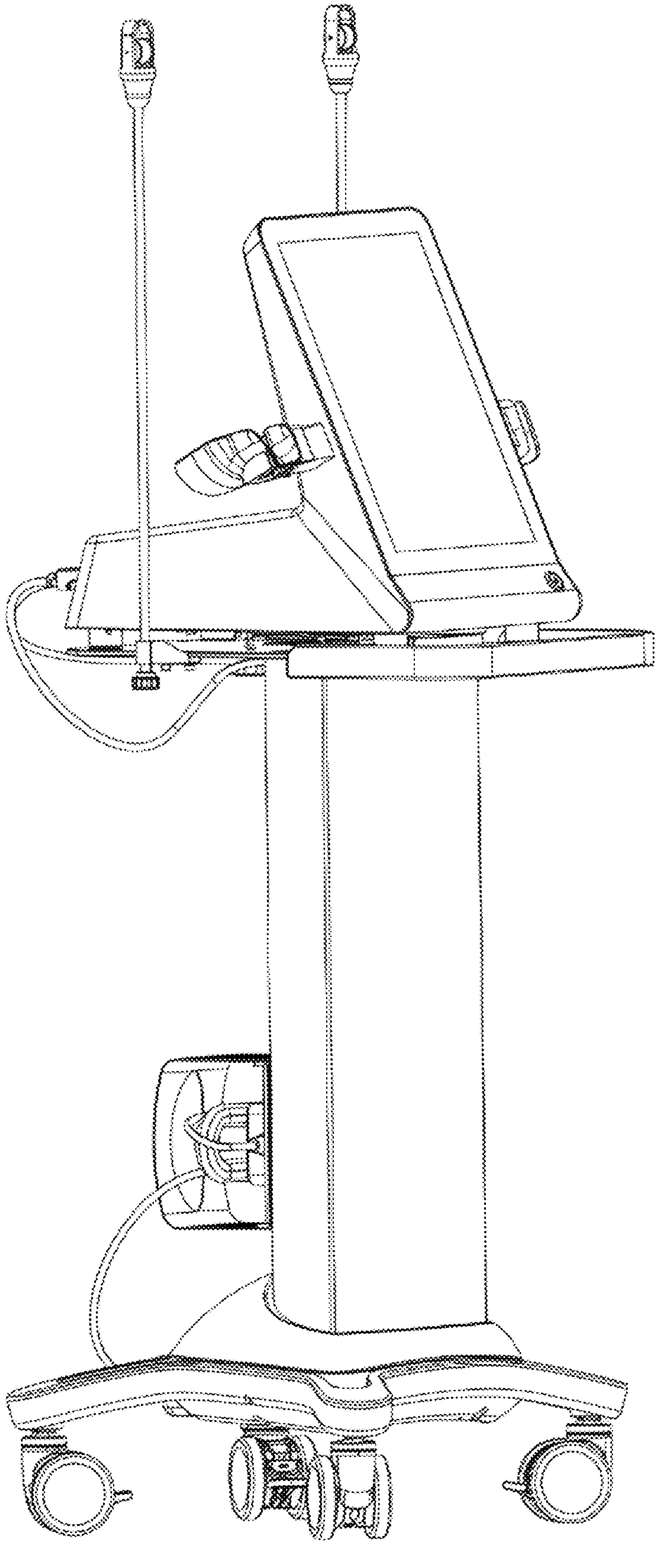
FIG. 15 is a structural schematic view of an ultrasonic therapeutic apparatus according to an embodiment of the present application.

In some embodiments, as shown in FIG. 15, the present application further relates to an ultrasonic therapeutic apparatus including the treatment handpiece as described above.

The above are only some embodiments of the present application, and are not intended to limit the scope of the present application. Under the concept of the present application, any equivalent structure transformation made by utilizing the description and accompanying drawings of the present application, or directly or indirectly applied in other related technical fields, is included within the scope of the present application.

What is claimed is:

1. A treatment handpiece, comprising:

a handpiece body; and a treatment tip, comprising:

an input shaft;

a transducer motion assembly comprising a rotary motion part and a linear motion part, wherein one end of the input shaft is connected to the rotary motion part, and the linear motion part is connected to the rotary motion part; and a transducer connected to the linear motion part;

wherein the input shaft drives the rotary motion part to rotate while the rotary motion part drives the linear motion part to linearly move, such that the transducer moves linearly, wherein the other end of the input shaft is provided with a second guiding element;

wherein the handpiece body comprises a driving assembly, the driving assembly is provided with a rotatable output shaft, and the output shaft is configured to connect and drive the input shaft of the treatment tip to rotate; a first end of the output shaft is provided with a first guiding element;

wherein the first guiding element comprises a plurality of bosses protruding from the first end, the plurality of the bosses are provided at intervals along a circumferential direction of the output shaft, and each of the bosses is extending along a radial direction of the output shaft; one end of the boss close to the treatment tip is formed with two guide surfaces, and one end of the boss away from the treatment tip is formed with two first transmission inclined surfaces; and the second guiding element comprises a plurality of protrusions provided at the opposite end of the input shaft, the plurality of the protrusions are provided at intervals along a circumferential direction of the input shaft, and two adjacent protrusions are enclosed to form a receiving groove for receiving the boss; two guide convex edges are formed at both sides of each protrusion, and two second transmission inclined surfaces with an included angle are formed between the two second guide convex edges.

2. An ultrasonic therapeutic apparatus, comprising the treatment handpiece according to claim 1.

3. The treatment handpiece according to claim 1, wherein the input shaft is configured to drive the rotary motion part to perform bidirectional reciprocating linear motion, a side of the rotary motion part facing the linear motion part is provided with a plurality of first tooth parts, and a side of the linear motion part facing the rotary motion part is provided with a plurality of second tooth parts; the plurality of the first tooth parts are meshed and connected with the plurality of the second tooth parts to drive the linear motion part to perform linear reciprocating motion.

4. The treatment handpiece according to claim 3, wherein an opposite side of the rotary motion part away from the plurality of first tooth parts is provided with a limit groove extending along a circumferential direction; the treatment tip further comprises a limit part, one end of the limit part is provided at the transducer, and an opposite end of the limit part is exposed at the limit groove to limit a rotation angle of the rotary motion part.

5. The treatment handpiece according to claim 4, wherein a side of the linear motion part facing the rotary motion part is provided with two second tooth parts, and the two second tooth parts are symmetrically provided at two sides of the rotary motion part; two sides of the transducer are respectively connected to the two second tooth parts to drive the transducer to perform linear reciprocating motion in a horizontal direction.

6. The treatment handpiece according to claim 1, wherein two linear motion parts are provided, and the two linear motion parts are symmetrically provided at two sides of the rotary motion part; the input shaft is configured to drive the rotary motion part to rotate solely towards one direction, and a side of the rotary motion part facing the two linear motion parts is partially provided with a plurality of third tooth parts; a side of the two linear motion parts facing the rotary motion part is provided with a plurality of fourth tooth parts, and the plurality of the third tooth parts are meshed and connected with the plurality of the fourth tooth parts to drive the two linear motion parts to perform linear reciprocating motion.

7. The treatment handpiece according to claim 1, wherein the first guiding element is connected and installed with the second guiding element such that the output shaft drives the input shaft to rotate while the input shaft drives the transducer motion assembly to move linearly.

8. The treatment handpiece according to claim 1, wherein:

a first chamfer is provided between the two first transmission inclined surfaces between two adjacent bosses; and a second chamfer is provided between the two second transmission inclined surfaces on a same protrusion, and the first chamfer and the second chamfer are connected with in interference fit.

9. The treatment handpiece according to claim 1, wherein:

an included angle between the two guide surfaces on the same boss is 10° to 120°; the guide surface comprises an inclined surface or a curved surface; and a first safety plane is provided at an intersection of the two guide surfaces on a same boss, and a width of the first safety plane is in a range of 0.01 mm to 2 mm.

10. The treatment handpiece according to claim 1, wherein each of the protrusions is further provided with two cutting inclined surfaces at an included angle, the guide convex edge is provided at a connection between one of the cutting inclined surfaces and one of the second transmission inclined surfaces, a second safety plane is provided at a connection area between the two cutting inclined surfaces, and a width of the second safety plane is 0.01 mm to 2 mm.

11. The treatment handpiece according to claim 1, wherein the handpiece body further comprises a sensor assembly, the sensor assembly is electrically connected to the driving assembly to detect and control a rotation angle of a driving shaft of the driving assembly, and the driving shaft is provided with a preset correction position.

12. The treatment handpiece according to claim 11, wherein the handpiece body further comprises a first limit part, and the first limit part is configured to limit the rotation angle of the driving shaft.

13. The treatment handpiece according to claim 11, wherein a side of the transducer motion assembly is connected to the other end of the input shaft and the opposite side of the transducer motion assembly is connected to the transducer such that a rotary motion of the input shaft is converted into a linear reciprocating motion of the transducer.

14. The treatment handpiece according to claim 13, wherein the transducer is provided with a preset position; in response to that the driving shaft being in the preset correction position is connected to the input shaft, the transducer returns to the preset position.

15. The treatment handpiece according to claim 14, wherein the treatment tip further comprises a second limit part, and the second limit part is configured to limit a displacement distance of the transducer.

16. The treatment handpiece according to claim 11, wherein:

the handpiece body further comprises a shaft sleeve, one end of the shaft sleeve is sleeved on the driving shaft, and a shielding part is provided at an outer peripheral wall of the shaft sleeve;

the sensor assembly is a photoelectric sensor assembly, the photoelectric sensor assembly is provided close to the shaft sleeve, and the shielding part is provided with a first state of blocking an optical signal of the photoelectric sensor assembly and a second state of avoiding the optical signal of the photoelectric sensor assembly; and two shielding parts are provided, and the two shielding parts are symmetrically provided at the outer peripheral wall of the shaft sleeve.

17. The treatment handpiece according to claim 16, wherein the handpiece body further comprises a shell and a bracket, the shell is provided with a receiving cavity and is provided with an avoiding hole for the driving shaft to pass through, the bracket is provided at the receiving cavity, and the driving assembly is provided at the receiving cavity and provided at the bracket.

18. The treatment handpiece according to claim 17, wherein:

the bracket comprises a base for fixing the driving assembly and a baffle plate connected to the base, and the baffle plate is parallel to an axial direction of the shaft sleeve; and the photoelectric sensor assembly comprises two supporting arms opposite to each other, a transmitting part and a receiving part, the two supporting arms are provided at intervals at the baffle plate, and the transmitting part and the receiving part are opposite to each other at the two supporting arms; when the shielding part is in the first state, the shielding part is provided between the transmitting part and the receiving part.

* * * * *